United States Patent
McKenzie et al.

(10) Patent No.: US 8,265,959 B2
(45) Date of Patent: Sep. 11, 2012

(54) PRESCRIPTION DRUG PRIOR AUTHORIZATION SYSTEM AND METHOD

(75) Inventors: Ronald Keith McKenzie, Louisville, KY (US); Sarah Stephens, Louisville, KY (US); Kathryn Knapp Broaddus, Louisville, KY (US); Brad Ennis, Crestwood, KY (US); Kristen R. Augspurger, Louisville, KY (US)

(73) Assignee: Humana Inc., Louisville, KY (US)

( * ) Notice: Subject to any disclaimer, the term of this patent is extended or adjusted under 35 U.S.C. 154(b) by 477 days.

(21) Appl. No.: 12/188,431

(22) Filed: Aug. 8, 2008

(65) Prior Publication Data

US 2009/0198518 A1      Aug. 6, 2009

Related U.S. Application Data

(60) Provisional application No. 61/025,148, filed on Jan. 31, 2008.

(51) Int. Cl.
  *G06Q 50/00* (2012.01)
(52) U.S. Cl. ..................................... 705/3; 705/2; 705/4
(58) Field of Classification Search .................... 705/2–4
  See application file for complete search history.

(56) References Cited

U.S. PATENT DOCUMENTS

| | | | |
|---|---|---|---|
| 6,088,677 A | | 7/2000 | Spurgeon |
| 2003/0055687 A1* | | 3/2003 | Rudy ................................ 705/4 |
| 2003/0139945 A1* | | 7/2003 | Brown et al. ..................... 705/2 |
| 2004/0006490 A1* | | 1/2004 | Gingrich et al. .................. 705/2 |
| 2006/0116907 A1* | | 6/2006 | Rhodes et al. .................... 705/2 |
| 2006/0178915 A1* | | 8/2006 | Chao ................................. 705/4 |
| 2008/0288407 A1* | | 11/2008 | Hamel et al. .................... 705/50 |
| 2009/0024412 A1* | | 1/2009 | Medvitz et al. .................. 705/2 |

OTHER PUBLICATIONS

ACS, SmartPA Prior Authorization Tool, brochure, 2 pages.
ACS: Informed Health: SmartPA, Nov. 12, 2007, http://www.acs-inc.com/informedhealth/smartpa.asp.

* cited by examiner

*Primary Examiner* — Lena Najarian
(74) *Attorney, Agent, or Firm* — Standley Law Group LLP

(57) ABSTRACT

An online application for approving prior authorization requests for prescription drugs. The application is used by pharmacy benefits providers, physicians, and pharmacies to request prior authorizations for drugs and to receive approvals automatically if a requested drug meets authorization criteria. The online application is accessible through a group pharmacy benefits provider portal on a web site. Requests are processed through a pharmacy benefits manager computer that determines whether prior authorization is required and through a pharmacy benefits provider computer when the pharmacy benefits manager computer determines that prior authorization is required. Requests that meet certain authorization criteria are approved automatically. Requests that cannot be approved automatically are submitted for review by a clinical pharmacy review division that access requests through a drug request transaction computer.

17 Claims, 7 Drawing Sheets

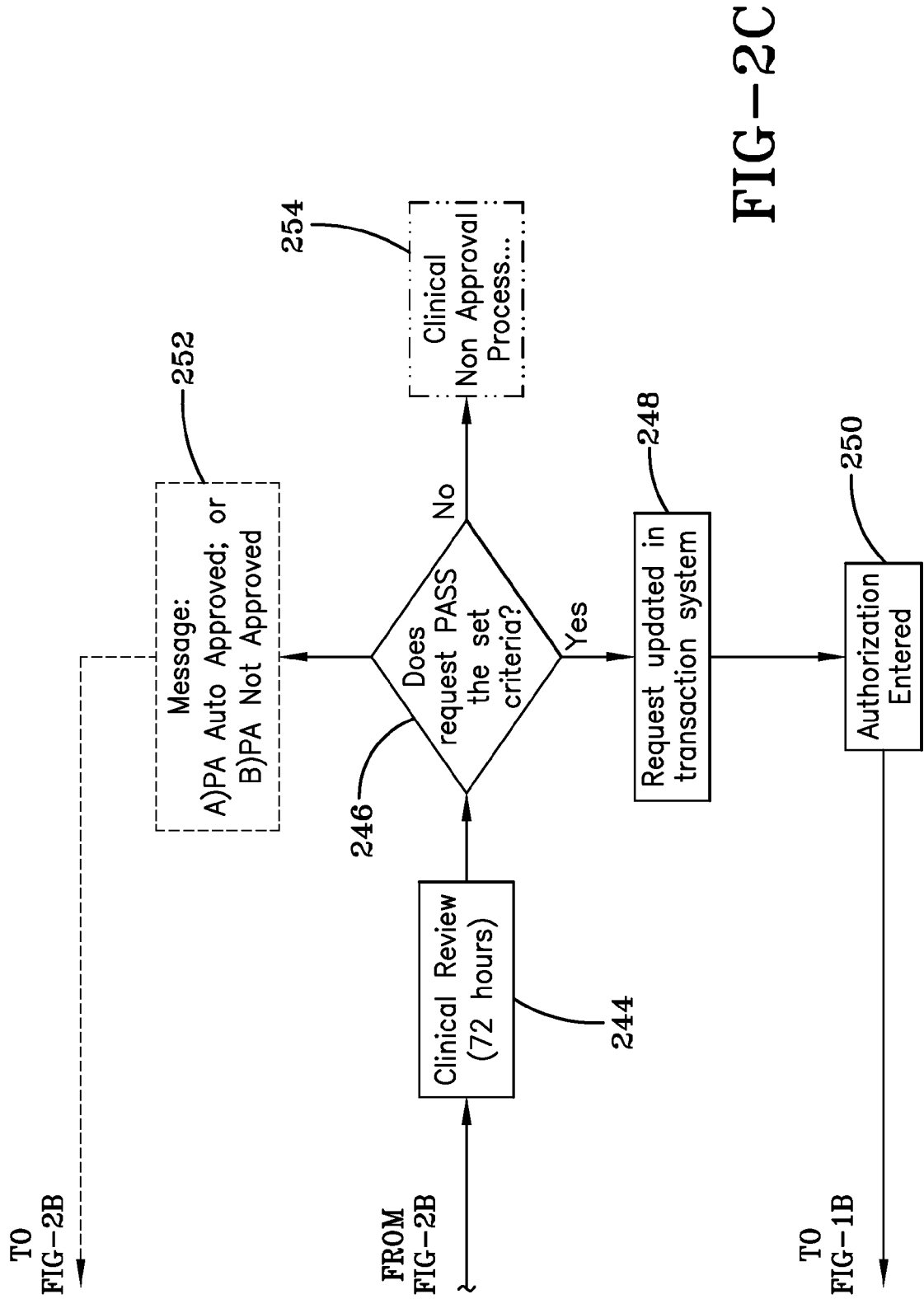

Pharmacy Benefits Manager Authorization Detail

Member ID Number: 00000001234567890 — 300

Override of DUR edit: x — 302

GCN: 00000 — 306

Refills: 000 /000 — 304

Authorization Date Range: 10/19/2006 to 00/00/0000 — 308

Quantity: 0.000 — 310

Days Supply: 000 — 312

FIG-3

PRESCRIPTION DRUG PRIOR AUTHORIZATION SYSTEM AND METHOD

CROSS-REFERENCE TO RELATED APPLICATIONS

This application claims the benefit of U.S. Provisional Patent Application No. 61/025,148, filed Jan. 31, 2008.

FIELD OF THE INVENTION

The present invention relates to prescription drug prior authorization systems and methods. In particular, the present invention is computerized prior authorization system and method that provides online, real-time prescription drug prior authorizations through multiple interfaces to a single, comprehensive authorization process.

BACKGROUND OF THE INVENTION

Prescription drug costs are contributing significantly to increases in overall U.S. healthcare spending. In an effort to control the escalating costs of prescription drugs, more and more pharmacy benefits providers are using Prior Authorization ("PA"). Prior authorization is a procedure that pharmacy benefits providers require physicians to follow when prescribing certain drugs to covered individuals. Physicians are asked to contact the pharmacy benefits provider in advance of prescribing certain drugs so that the provider can approve the request prior to the covered individual receiving the prescribed drug.

Pharmacy benefits providers require PA for a variety of reasons. They may ask the physician to provide documentation regarding the patient and the requested drug to verify the medical necessity of the drug and to ensure the appropriate physician is prescribing the drug and providing related services. Authorization criteria may vary depending upon the benefits that are available to the covered individual. Some pharmacy benefit plans have "closed formulary benefits" such that certain drugs are not covered under the plan. PA requirements allow the pharmacy benefits provider to confirm that the requested drug is covered by the individual's plan or that is prescribed for a condition that is covered. Other pharmacy benefits providers require PA for specialized drugs or drugs that have a potential for overuse or misuse or that may be used longer or in higher quantities than are recommended. For some drugs, a less expensive alternative may be available. Some drugs may have limited uses based on studies or FDA approval. Certain drugs may be subject to medical diagnostic tests to ensure a medical benefit. PA requirements allow the pharmacy benefits provider to monitor the usage of such drugs to meet a variety of conditions.

Finally, some pharmacy benefits providers have developed "step therapy" programs that require covered individuals to try generic or less potent drugs before trying other drugs. PA may be used to ensure the physician and covered individual follow the appropriate steps in the program. The provider may ask the physician to provide proof of treatment failure or significant adverse reaction to drugs prescribed initially before authorizing drugs in a later step of the program.

Although PA provides cost-savings to pharmacy benefits providers and their covered individuals, the approach also involves an administrative overhead that reduces the potential of the costs-savings. Many pharmacy benefits providers use the services of a group pharmacy benefits provider such as Humana Inc. The pharmacy benefits or network providers work with a group provider that assists with implementation of a PA program that meets the needs of the network provider. PA involves one-on-one communication between a physician and a representative of a pharmacy benefits or network provider. The network provider may rely on a clinical pharmacy review division of the group provider to determine whether certain requests meet the authorization criteria of the network provider.

Requests are submitted by fax or telephone to the group provider's clinical pharmacy review division where a representative reviews the request and the applicable plan details to determine whether the request meets the authorization criteria for the network provider. The volume of requests forwarded to the clinical pharmacy review division is substantial. For example, in a given day, Humana's clinical pharmacy review division handles approximately 6500 inbound contacts, 2000 by fax and 4500 by telephone call. As many as 80% of the requests it receives are from the pharmacy benefits providers.

One way to reduce the administrative burden is to streamline and automate the PA process. Automation requires appropriate computer communications between the prescribing physician, the pharmacy benefits or network provider, the pharmacy filling the prescribed drug, and in many instances, a clinical pharmacy review division. Computer technology has been applied to the PA process to automate certain aspects of it. Such systems, however, typically allow only one party such as a pharmacist to submit a PA drug request. Furthermore, if the drug request is not approved through the computer system, the pharmacist must call a live agent to discuss the request. There is a need for a PA computer system that provides online, real-time prescription drug prior authorizations through multiple interfaces to a comprehensive authorization process. There is a need for PA computer system that provides online, real-time prescription drug prior authorizations to multiple users such as pharmacy benefits providers, physicians, and pharmacies. The average cost per contact using current fax and telephone methods is estimated to be $7. With a 25% annual reduction in provider contacts for prior authorization through live agents, the estimated savings potential for one year for a group benefits provider could be $1.74M.

SUMMARY OF THE INVENTION

The present invention is a self-service, online application for pharmacy benefits providers, physicians, and pharmacies that allows 24 hour access to request prior authorizations online and receive approvals automatically if a requested drug meets authorization criteria. In an example embodiment of the present invention, the authorization process is comprehensive and is the same for all drug requests with appropriate information directed to each user. The features and functionality of the online application of the present invention are available through a group provider portal on a web site (e.g., humana.com).

The PA portal and online application of the present invention provides pharmacy benefit network providers with an easy to use and more time efficient and effective method to request PAs for commonly prescribed drugs. The PA portal and online application further reduce the need to manually process requests through a clinical pharmacy review division. The PA portal facilitates submission of PA requests to the online application that authorizes prescription drugs according to authorization criteria for a pharmacy benefits plan. The online application further complies with Center for Medicare and Medicaid Services ("CMS") and other regulatory guidelines to provide such tools for prior authorization.

In an example embodiment of the present invention, network providers use the PA provider portal to submit requests on frequently prescribed drugs that require a prior authorization. The online application prompts a user for member information that is submitted to a member eligibility subsystem to confirm eligibility and the applicable plan. The user then follows a series of prompts and provides information regarding the requested drug and reason for a PA. The user's answers determine whether the authorization can be provided automatically because it meets the authorization criteria for the drug and plan or whether the request needs to be submitted to a clinical pharmacy review division for approval. For approvals provided automatically or by the review division, the online application completes a transaction with a pharmacy benefits manager computer to permit a pharmacy to the access the request for the drug when the covered individual fills the prescription. A form letter confirming the transaction may be generated and sent upon completion of the transaction. Automatic denials are directed to the drug request transaction computer system which is accessible via a portal for the network provider. All transactions and attendant results are logged with a specific category, reason, and disposition.

BRIEF DESCRIPTION OF THE DRAWINGS

FIGS. 2A-2C are a schematic diagram of a second system for providing prior authorization for prescription drugs according to an example embodiment of the present invention.

FIG. 3 is a screen shot for communicating drug request information to a PBM.

DETAILED DESCRIPTION

Figure 1A:
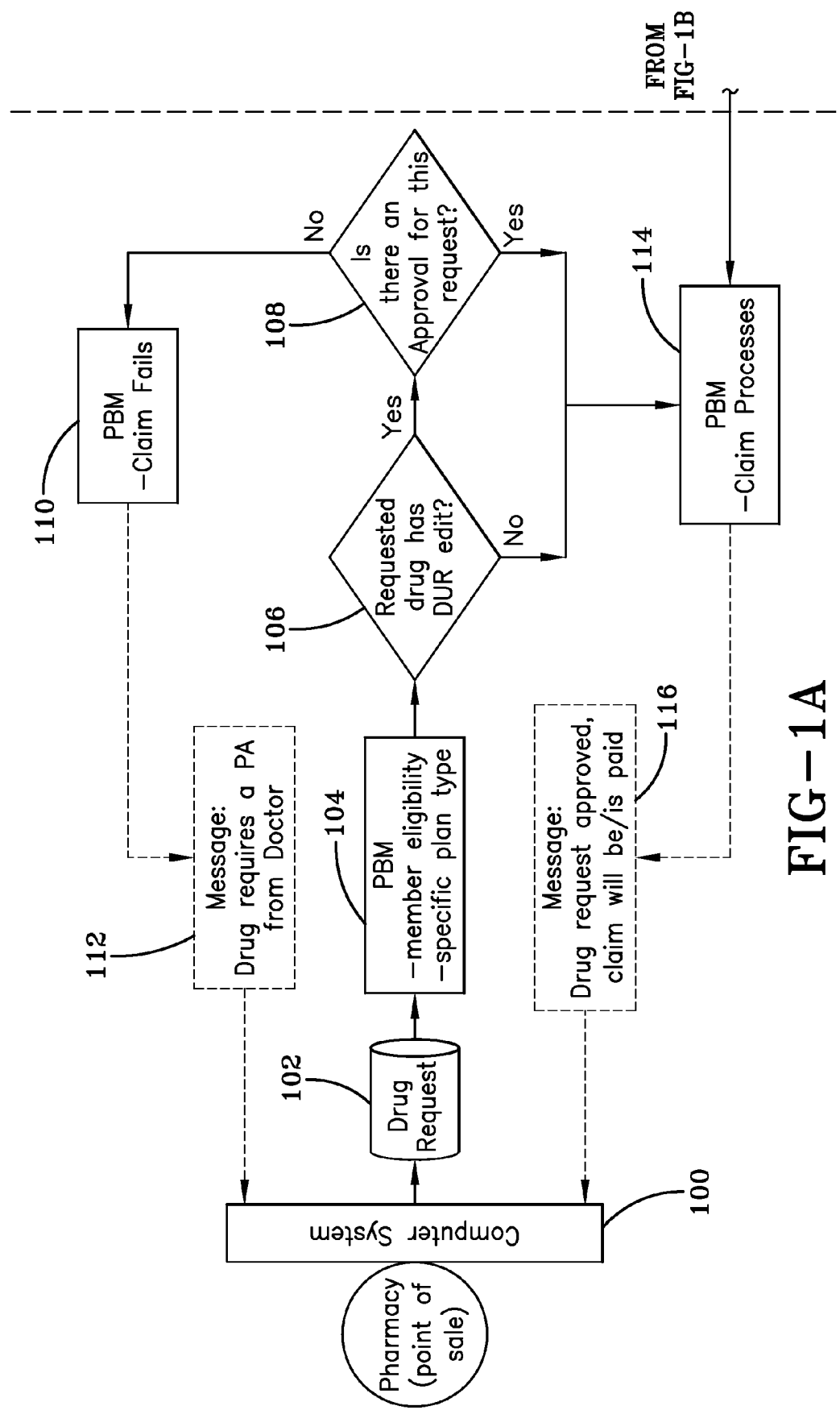
FIGS. 1A-1C are a schematic diagram of a first system for providing prior authorization for prescription drugs according to an example embodiment of the present invention.
Figure 1B:
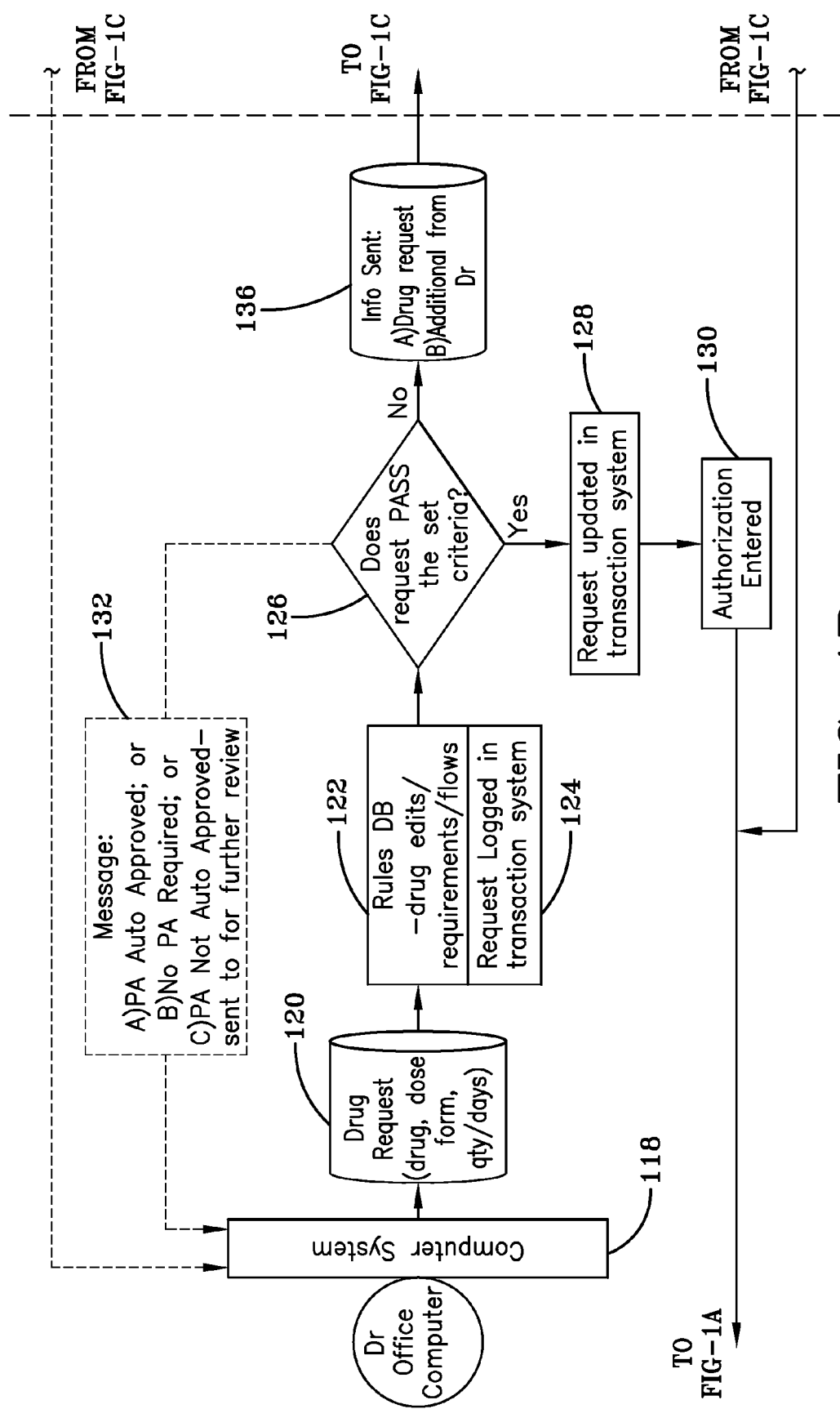

Referring to FIG. 1B, a first system for providing prior authorization for prescription drugs according to an example embodiment of the present invention is shown. A physician uses a computer 118 to submit a PA drug request 120 to a rules database server 122. The drug request 120 comprises member identifying data, drug identifying data as well as dosage, form, and quantity information. The rules database server 122 may be part of a group provider computer system such as one operated by Humana. The rules database server 122 and compares the drug request to rules related to the member's plan benefits and PA criteria. The drug request is also logged in a drug request transaction computer system 124 so that information about the drug request transaction can be recorded and accessed for later retrieval (e.g., by a representative of a clinical pharmacy review division). The rules database server 122 applies the authorization criteria to the drug request 126. If the drug request meets the authorization criteria, the drug request transaction logged in the drug request transaction computer system is updated 128 and an authorization transaction 130 is communicated to a pharmacy benefits manager computer system 114 accessible to the pharmacy where the member fills prescriptions. The prescribing physician is also notified that the drug request was approved 132.

Figure 1C:
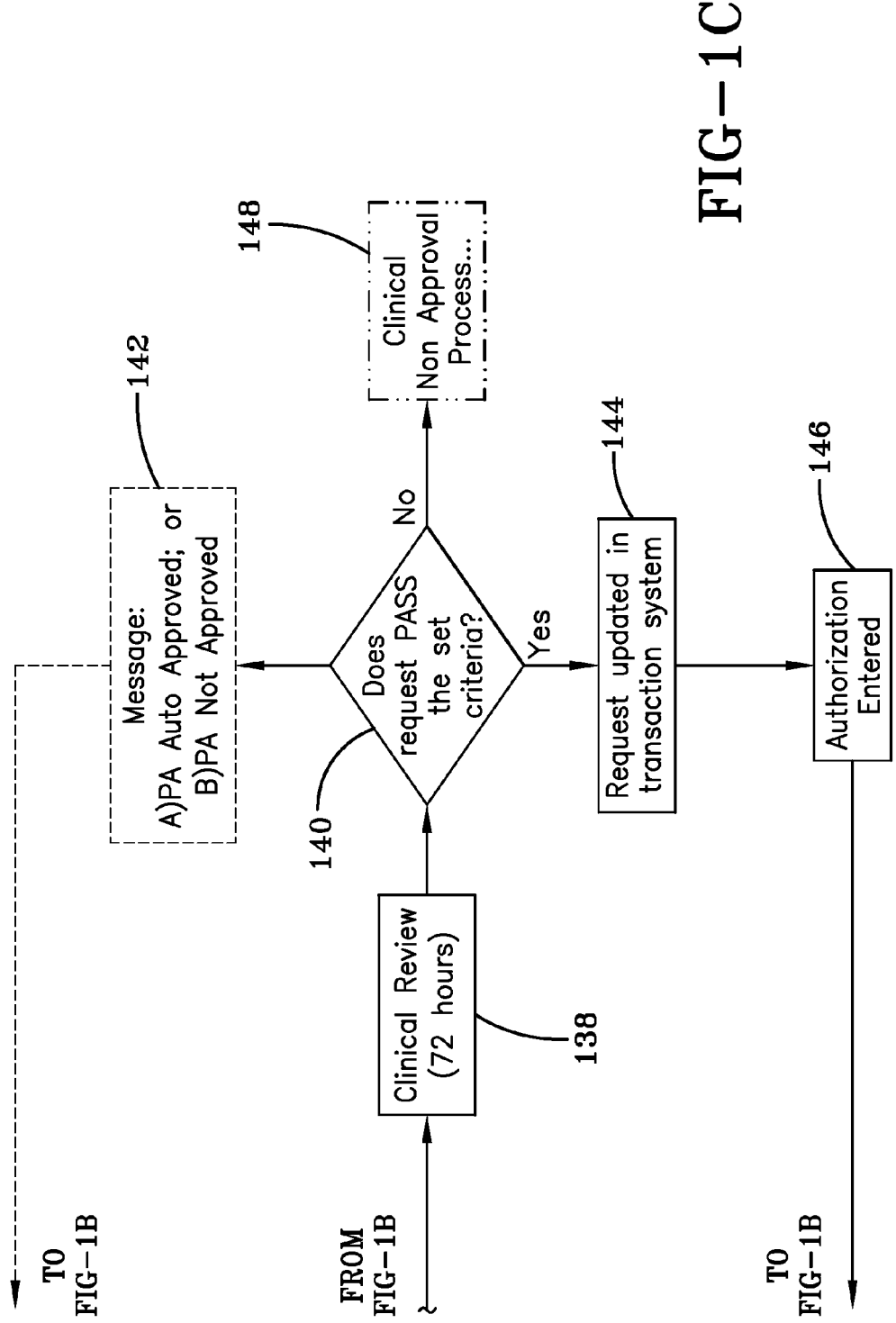

If the drug request does not meet the authorization criteria, it is submitted for review 136 to a clinical pharmacy review division 138 (FIG. 1C). Referring to FIG. 1C, the reviewer accesses the logged transaction from the drug request transaction computer system. The reviewer may request additional information from the physician and complete an assessment of the drug request and appropriate authorization criteria 140.

If the drug request meets the authorization criteria, the drug request transaction logged in the drug request transaction computer system is updated 144 with the approval decision and an authorization transaction 146 is communicated to a pharmacy benefits manager computer system 114 (FIG. 1A) accessible to the pharmacy where the member fills prescriptions. The prescribing physician is also notified that the drug request was submitted for review and approved or approved 142. If the reviewer determines that the drug request does not meet the authorization criteria, it is submitted to a clinical pharmacy review non-approval process 148 and the prescribing physician is notified of the non-approval 142.

A physician may also be notified that no prior authorization is required with a "No PA required" message. This information is very valuable because the physician does not need spending time obtaining authorization for the request and can send the patient to the pharmacy immediately. In addition, no provider resources are required to inform the physician that no prior authorization is required. This message therefore, limits unnecessary work by both parties.

Referring to FIG. 1A, when the member goes to the pharmacy to receive the prescribed drug, a pharmacist uses a computer 100 to process the drug request 102. The drug request comprising the member identifying data, drug identifying data as well as dosage, form, and quantity information 102 is submitted to a pharmacy benefits manager computer system 104 where the member's eligibility and plan information is confirmed. The computer system 104 checks to determine whether a drug utilization review (DUR) 106 is required. If a DUR is not required, the claim is processed by the pharmacy benefits manager 114 and a message indicating the drug request is approved and the claim will be paid is communicated to the pharmacist 100.

If a DUR is required, the pharmacy benefits manager then determines whether PA for the requested drug has been obtained 108. If PA is required and has not been obtained, the claim fails 110 and the pharmacist is notified that PA for the drug is required 112. If the PA for the drug request has been obtained through the rules database server 122 or the clinical pharmacy review division 138 (FIG. 1C), the claim is approved 114 and the pharmacist is notified that the drug request has been approved and the claim will be paid by the provider 116.

Figure 2A:
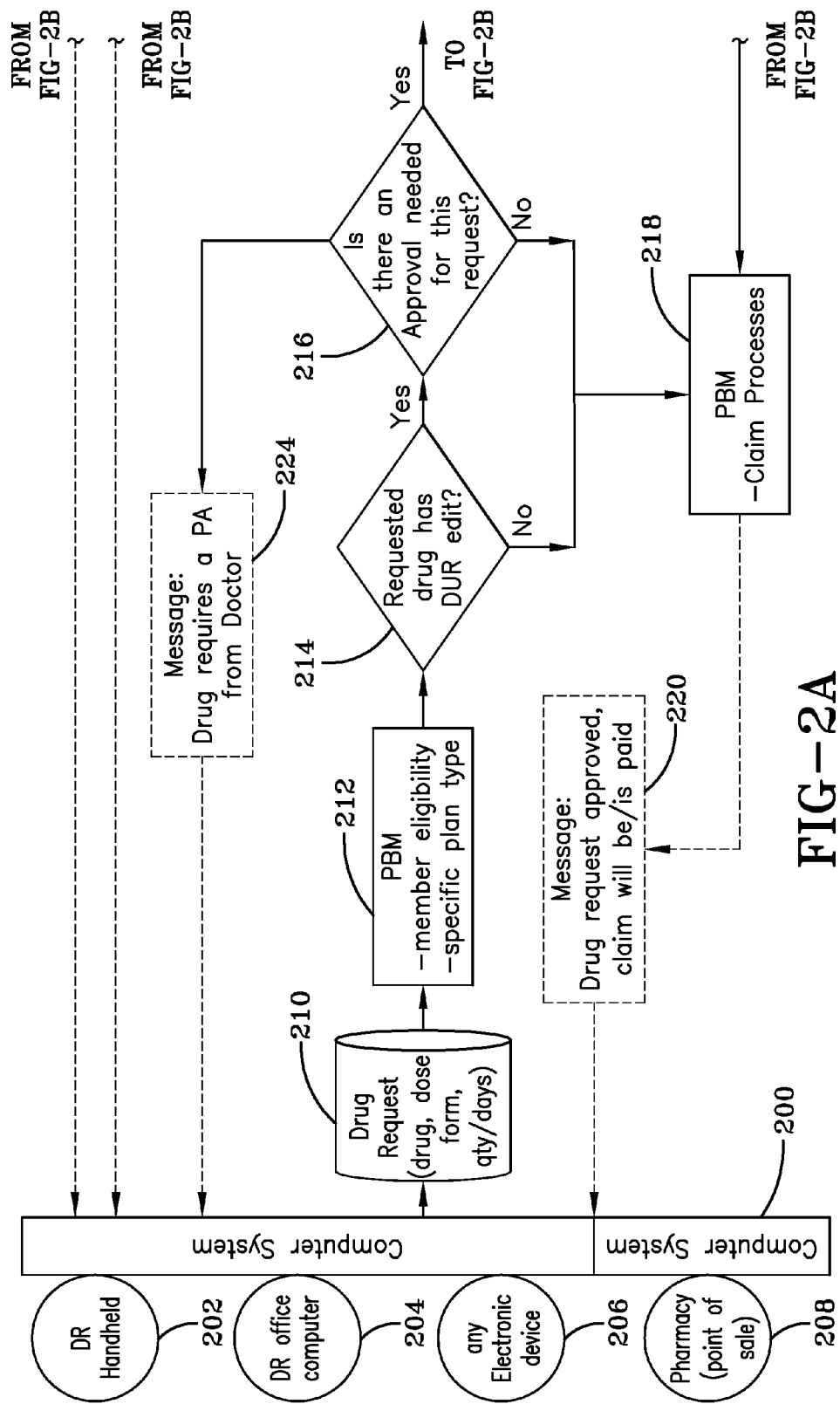

Referring to FIG. 2A, a schematic diagram of a second system for providing prior authorization for prescription drugs according to an example embodiment of the present invention is shown. A computer system 200 for submitting PA drug requests accept request information from a plurality of devices including a physician's handheld device 202, a physician's office computer 204, or any type of electronic device 206. The computer system also accepts request input from a pharmacy point-of-sale computer system 208. In an example embodiment of the present invention, users direct a browser to a web portal where drug requests are input and approval status information is provided in response to the requests.

When a physician requests access to the PA online application 202, 204, the online application first identifies the provider office, and then the specific physician prescribing the medication. A user is asked to provide a proper log-on to access a secured section of a provider portal with access to the PA online application. By entering through the provider portal, the online application may be provided with the provider office tax identification number to facilitate processing of the drug request. The application then provides the user with a list of physicians associated with the tax identification number. The user selects the physician and enters contact information such as an office phone number and fax number.

Physicians submitting PA drug requests 210 begin the PA auto approval process by entering member eligibility information such as a member or subscriber identifier and plan type so the member's eligibility and specific pharmacy benefits plan data can be confirmed. The online application may comprise an input area for a member or subscriber identification information such as a number. One or more persons may be associated with the identification information. The physician may be asked to select one of the persons associated with the identification information for whom the PA drug request will be made.

Member eligibility information is processed through a pharmacy benefits manager (PBM) 212. The PBM 212 uses the member identification information and other identifying information such as the person's name to verify eligibility and to determine the specific pharmacy benefits plan parameters applicable to the drug request. If the eligibility check fails, the physician is notified that the member does not have pharmacy benefits. If the PBM 212 determines the member is eligible, the authorization process continues.

The drug request further comprises drug identifying information as well as dose, form, and quantity or number of days. In an example embodiment of the present invention, the physician user interface may prompt the physician to select a drug from a "Prior Authorization Required Drug List/Selection." The list may comprise frequently prescribed PA required drugs. An example of a PA drug list is shown in Table 1.

TABLE 1

Prior Authorization Drug List

| Drug | Dose and Form Options |
|---|---|
| Aciphex | Aciphex 20 mg---30 tablets/30 days |
| Atacand | Atacand 4 mg---60 tablets/30 days |
|  | Atacand 8 mg---60 tablets/30 days |
|  | Atacand 16 mg---60 tablets/30 days |
|  | Atacand 32 mg---30 tablets/30 days |
| Atacand HCT | Atacand HCT 16-12 mg---30 tablets/30 days |
|  | Atacand HCT 32-12 mg---30 tablets/30 days |
| Avalide | Avalide 150/12.5 mg---30 tablets/30 days |
|  | Avalide 300/12.5 mg---30 tablets/30 days |
|  | Avalide 300/25 mg---30 tablets/30 days |
| Avapro | Avapro 75 mg---30 tablets/30 days |
|  | Avapro 150 mg---30 tablets/30 days |
|  | Avapro 300 mg---30 tablets/30 days |
| Benicar | Benicar 5 mg---30 tablets/30 days |
|  | Benicar 20 mg---30 tablets/30 days |
|  | Benicar 40 mg---30 tablets/30 days |
| Benicar HCT | Benicar HCT 20-12.5 mg---30 tablets/30 days |
|  | Benicar HCT 40-12 mg---30 tablets/30 days |
|  | Benicar HCT 40-25 mg---30 tablets/30 days |
| Byetta Injections | 5 mcg - 1.2 ml pre-filled pen every 30 days (this contains 60 doses) |
|  | 10 mcg - 2.4 ml pre-filled pen every 30 days (this contains 60 doses) |
| Celebrex | Celebrex 100 mg - 60 caps/30 days |
|  | Celebrex 200 mg - 60 caps/30 days |
| Cozaar | Cozaar 25 mg---60 tablets/30 days |
|  | Cozaar 50 mg---60 tablets/30 days |
|  | Cozaar 100 mg---60 tablets/30 days |
| Diovan | Diovan 40 mg---60 tablets/30 days |
|  | Diovan 80 mg---60 tablets/30 days |
|  | Diovan 160 mg---60 tablets/30 days |
|  | Diovan 320 mg---60 tablets/30 days |
| Diovan HCT | Diovan HCT 80-12.5 mg---30 tablets/30 days |
|  | Diovan HCT 160-12.5 mg---30 tablets/30 days |
|  | Diovan HCT 160-25 mg---30 tablets/30 days |
|  | Diovan HCT 320-12.5 mg---30 tablets/30 days |
|  | Diovan HCT 320-25 mg---30 tablets/30 days |
| Hyzaar | Hyzaar HCT 50-12.5 mg---60 tablets/30 days |
|  | Hyzaar HCT 100-25 mg---60 tablets/30 days |
| Lamisil | Lamisil 250 mg---30 tablets/30 days |
| Meloxicam | Meloxicam 7.5 mg---30 pills/30 days |

TABLE 1-continued

Prior Authorization Drug List

| Drug | Dose and Form Options |
|---|---|
|  | Meloxicam 15 mg---30 pills/30 days |
| Micardis | Micardis 20 mg---30 tablets/30 days |
|  | Micardis 40 mg---30 tablets/30 days |
|  | Micardis 80 mg---60 tablets/30 days |
| Micardis HCT | Micardis HCT 40-12.5 mg---30 tablets/30 days |
|  | Micardis HCT 80/12.5 mg---60 tablets/30 days |
|  | Micardis HCT 80/25 mg---60 tablets/30 days |
| Mobic | Mobic 7.5---30 tabs/30 days |
|  | Mobic 15---30 tabs/30 days |
|  | Mobic 7.5/5 ml oral suspension---300 ml's/30 days |
| Nexium | Nexium 20 mg---30 capsules/30 days |
|  | Nexium 40 mg---30 capsules/30 days |
| Norvasc | Norvasc 2.5 mg---30 tablets/30 days |
|  | Norvasc 5 mg---30 tablets/30 days |
|  | Norvasc 10 mg---30 tablets/30 days |
| Omeprazole | Omeprazole 10 mg---30 capsules/30 days |
|  | Omeprazole 20 mg---30 capsules/30 days |
| Plendil | Plendil 2.5 mg---30 tablets/30 days |
|  | Plendil 5 mg---30 tablets/30 days |
|  | Plendil 10 mg---30 tablets/30 days |
| Prevacid | Prevacid 15 mg---30 solutabs/30 days |
|  | Prevacid 30 mg---30 solutabs/30 days |
|  | Prevacid 15 mg---30 capsules/30 days |
|  | Prevacid 30 mg---30 capsules/30 days |
|  | Prevacid 15 mg---30 suspension/30 days |
|  | Prevacid 30 mg---30 suspension/30 days |
|  | Prevacid NapraPAC---84 capsules/tabs/30 days |
| Prilosec | Prilosec 10 mg---30 capsules/30 days |
|  | Prilosec 20 mg---30 capsules/30 days |
|  | Prilosec 40 mg---30 capsules/30 days |
| Protonix | Protonix 20 mg---30 tablets/30 days |
|  | Protonix 40 mg---30 tablets/30 days |
| Teveten | Teveten 400 mg---60 tablets/30 days |
|  | Teveten 600 mg---60 tablets/30 days |
| Teveten HCT | Teveten HCT 600-12.5 mg---60 tablets/30 days |
|  | Teveten HCT 600-25 mg---60 tablets/30 days |
| Zegerid | Zegerid 20 mg---30 packets/30 days |

Following selection of a drug from the list results, the physician is prompted to respond to a series of questions regarding the requested drug (drug flow questions) to facilitate auto-approval of the drug for a PA transaction at a pharmacy. Table 2 lists a series of example drug flows organized by condition.

TABLE 2

Example Drug Flows

| Condition | Drug Flow |
|---|---|
| PPI/Heartburn Flow: | Aciphex |
|  | Nexium |
|  | Omeprazole |
|  | Prevacid |
|  | Prilosec |
|  | Protonix |
|  | Zegerid |
| Blood Pressure Flow: | Atacand |
|  | Atacand HCT |
|  | Avalide |
|  | Avapro |
|  | Benicar |
|  | Benicar HCT |
|  | Cozaar |
|  | Diovan |
|  | Diovan HCT |
|  | Hyzaar |
|  | Micardis |
|  | Micardis HCT |
|  | Norvasc |
|  | Plendil |
|  | Teveten |

TABLE 2-continued

Example Drug Flows

| Condition | Drug Flow |
|---|---|
| Cox-2/Mobic Flow: | Teveten HCT |
| | Celebrex |
| | Meloxicam |
| | Mobic |
| NSADs: | Anaprox |
| | Ansaid |
| | Arthrotec |
| | Cataflam |
| | Clinoril |
| | Daypro |
| | Diclofenac |
| | Etodolac |
| | Feldene |
| | Fenoprofen |
| | Fluribiprofen |
| | Ibuprofen |
| | Indocrin |
| | Indomethacin |
| | Ketaprofen |
| | Ketorolac |
| | Meloxicam |
| | Nabumetone |
| | Naprelan |
| | Naprosyn |
| | Naproxen |
| | Oxaprozin |
| | Piroxicam |
| | Relafen |
| | Sulindac |
| | Tolmetin |
| | Voltaren |
| Byetta/Symlin Flow: | Byetta Injections |
| Lamisil Flow: | Lamisil |

The physician provides information that allows the online application to communicate with the PBM 218. Referring to FIG. 3, a sample screen for communicating drug request information to the PBM 218 is shown. The physician provides the member identifier 300 and a request category 302 (e.g., a DUR edit that will result in determining whether prior authorization is required). The physician further provides the drug identifier 306 (such as a generic code number (GCN)), number of refills 304, approval end date 308, quantity 310, and quantity/days supply 312. The quantity is per drug and the days supply is per flow. Refills are also per flow. Codes such as the following may be used to indicate refills: lifetime duration=99999; 1 year=13 fills; 6 months=7 fills; and 3 months=4 fills. If the physician is unable to answer the questions or the answers are not sufficient to provoke auto-approval of the PA request, the physician may be provided with a telephone number, email address, or other contact information to complete the authorization process.

Referring again to FIG. 2A, in the next step of the PA process, a drug utilization review (DUR) 214 is completed. If the requested drug does not have a DUR edit, the drug is not subject to prior authorization and the request is processed through the PBM claim process 218. A message indicating the drug request is approved and the claim will be paid is communicated to the physician (and later to the pharmacist when the member fills the prescription). If the requested drug has a DUR edit, the PBM 212 checks next to see if a PA is required 216. If there is no PA requirement, the request is processed through the PBM claim process 218 and a message indicating the drug request is approved and the claim will be paid is communicated to the physician (and later to the pharmacist when the member fills the prescription). If PA is required, a message is communicated to the physician 224 and the PA process continues.

Figure 2B:
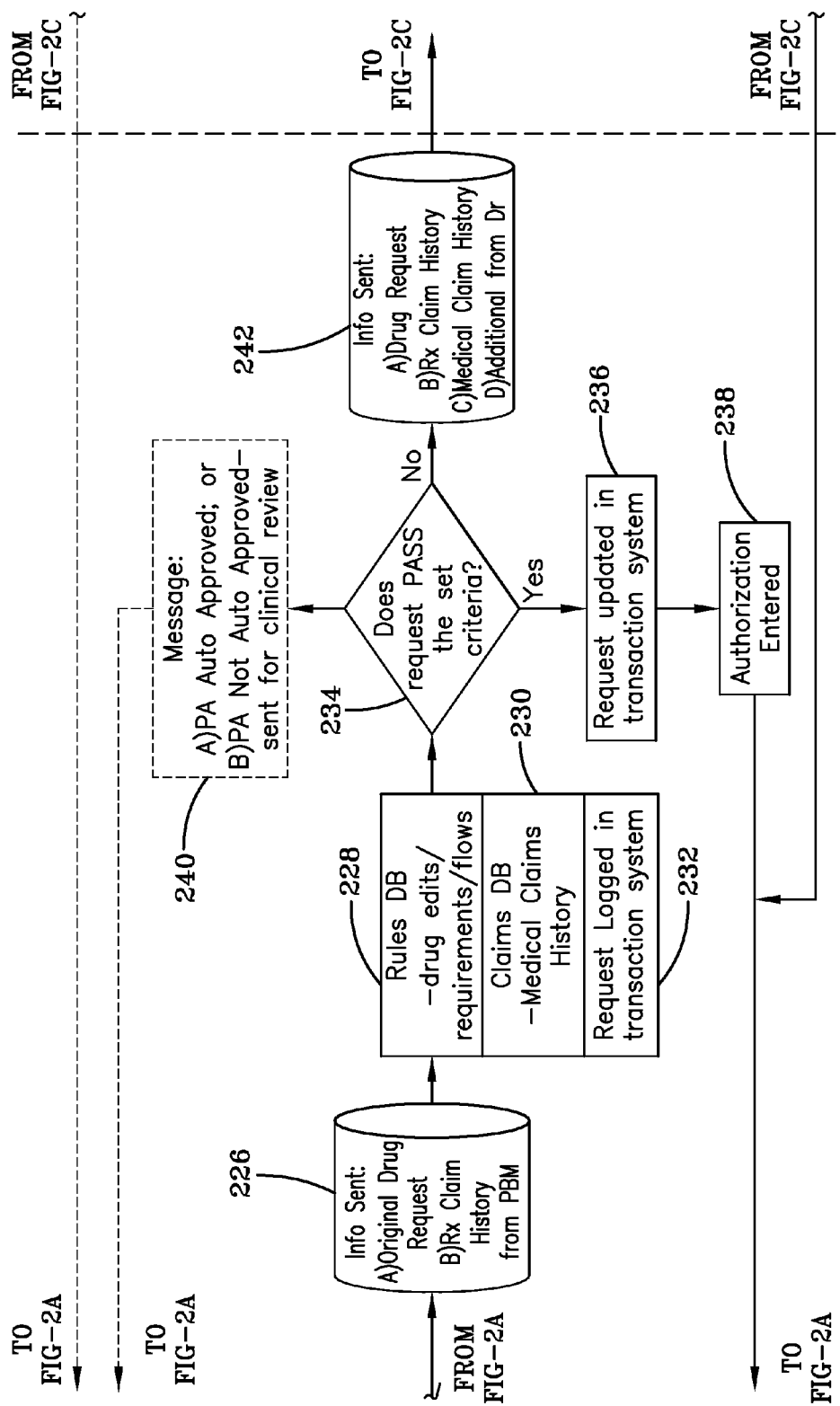

Referring to FIG. 2B, the PA process continues by submitting drug request data 226 to the rules database server for application of the PA rules 228. The drug request is recorded in a claims database 230 that comprises information about each member's medical claims history. When the drug request 226 is forwarded to the rules database server 228, a request to access a drug request transaction computer system is also initiated 232 so that information about the drug request transaction can be transmitted and recorded in a database. A contact history record is recorded in the drug request transaction computer system for all transactions processed through the PA online application. This information is used by the clinical pharmacy review division and customer service to complete the non-auto approved cases, to track approved cases, and to troubleshoot incoming questions about the transactions via customer calls. Each transaction may have a category, reason, and disposition. Table 3 provides a list of categories, reasons, and dispositions that may be recorded in a transaction record logged in the drug request transaction computer system.

TABLE 3

Category, Reason, Disposition Examples

| Category | Reason | Disposition |
|---|---|---|
| Web Exception | MDL; MDL/Step therapy; Step therapy | Web approval, Available 8x, Pending information |
| Web Prior Authorization-Commercial | MDL; MDL/MYB; MYB | Web approval, Refer to Fax; Available |
| Web Coverage Determination | Prior Authorization (PA) | Web approval, Pending information; Available |

A software application at the rules database server 228 applies the authorization criteria to the drug request 234. If the drug request meets the authorization criteria, the drug request transaction logged in the drug request transaction computer system is updated to reflect the auto-approval decision 236. An authorization transaction 238 is communicated to the PBM 212 accessible to a pharmacy 208 where the member fills the prescription. The physician may be notified that the drug request successfully completed the PA auto-approval process 240.

If the drug request does not meet the auto-approval authorization criteria, it is submitted for review to a clinical pharmacy review division 242. The prescribing physician may be notified that the drug request did not complete the auto-approval process and has been submitted to a clinical pharmacy review division for further consideration 240. The review request 242 comprises the original drug request and prescription claim history from the PBM 212 as well as medical claim history from a provider database 230. Additional information from the member's physician may also accompany the review request 242.

Referring to FIG. 2C, the reviewer accesses the transaction from the drug request transaction computer system 244 and applies the authorization criteria 246 using the prescription claim data and medical claim data if necessary. If the drug request meets the authorization criteria, the drug request transaction logged in the drug request transaction computer system is updated to reflect the approval decision 248 and an authorization transaction 250 is communicated to the PBM claim process 218 accessible to the pharmacy where the member fills prescriptions. The prescribing physician is notified that the drug request is approved 252. If the reviewer determines that the drug request does not meet the authorization criteria, it is submitted to a clinical pharmacy review denial process 254. The prescribing physician is notified that the drug request is not approved 252. The transaction and attendant results are logged in the drug request transaction computer system with a specific category, reason, and disposition. A form letter confirming the transaction and results may be generated and sent upon completion of the transaction.

Referring to Tables 4-8, details of user interface screens for a PA online application according to an example embodiment of the present invention are shown. Web pages for provider selection, member selection, drug selection, and flow and decision pages ("approved," "unapproved," and "not required") are dynamically generated based on user information and stored. The drug request transaction computer system comprises a complete contact history for PA drug requests made through the online application. Users of the transaction computer system include clinical review users for non-auto approved transactions and other customer care service representatives.

Table 4 illustrates details of an authorization request table that provides a list of all PA requests entered in the transaction computer system. Each transaction that is logged in the computer system is assigned a reference number. The provider, member, and PA drug identified in the request is associated with the reference number. Each reference number may be displayed as a hyperlink that when selected, results in the display of a PA request detail page as illustrated in Table 5.

TABLE 4

PA Request List

| Reference # | Provider | Member | Drug |
|---|---|---|---|
| 1646 949633575814 | A | 100 | ACIPHEX 20 MG TABLET EC |
| 1645 PA00001645996 | A | 244 | PROTONIX 40 MG TABLET EC |
| 1644 PA00001644277 | A | 678 | JANUMET 50-1,000 MG TABLET |
| 1643 PA00001643842 | B | 953 | JANUVIA 100 MG TABLET |
| 1642 PA00001642691 | B | 441 | JANUMET 50-1,000 MG TABLET |
| 1641 PA00001641472 | A | 548 | JANUMET 50-500 MG TABLET |
| 1640 PA00001640469 | C | 732 | PROTONIX 40 MG TABLET EC |
| 1639 PA00001639432 | D | 907 | ROZEREM 8 MG TABLET |
| 1638 PA00001638132 | A | 467 | JANUVIA 100 MG TABLET |
| 1637 PA00001637692 | A | 288 | ROZEREM 8 MG TABLET |
| 1636 PA00001636705 | D | 234 | LYRICA 75 MG CAPSULE |

Table 5 illustrates a PA request detail page. The top portion of the page lists details about a particular transaction identified by a reference number that is generated at the transaction time of the online PA request (e.g., 94963357814). It further lists information about the length of authorization (e.g., indefinitely), the provider, member, drug, related diagnosis and drug flow, and timestamp for the date the transaction was processed.

TABLE 5A

PA Request Detail Page - Reference Details

| | |
|---|---|
| Reference Number: | 949633575814 |
| ID: | 1646 |
| Final Step: | -6 Authorize indefinitely |
| Provider | A |
| Member: | 908 |
| Drug: | 62856024330 ACIPHEX 20 MG TABLET EC 30/30 |
| Diagnosis: | Erosive Esophagitis, test2, Weight Loss, Biopsy, Other, Ticlid/Plavix |
| Flow: | 21 Version 3.00 (PPI/Heartburn 2008) |
| Date Processed: | 1/8/2008 2:58:51 PM |

Another portion of the page list details about request processing and external interfaces to other computer systems involved in request processing. The page identifies each external system and provides status information along with a timestamp relevant to the transaction's processing. For example, the page shows when the transaction was entered in the transaction database and when the authorization was entered in the pharmacy benefits manager computer system.

TABLE 5B

PA Request Detail Page - External Systems

| System | Status | Last Update |
|---|---|---|
| Message Systems: | Queued for later processing Pending scheduled batch process | 1/8/2008 2:58:59 PM |
| Transaction Database: | Successfully processed Result: 949633575814 | 1/8/2008 2:58:58 PM |
| PBM Prior Authorization: | Successfully processed Received: success code = OO, ID = 35637125, paNumber = 35637125 | 1/8/2008 2:58:56 PM |

Another portion of the page shows the evaluation criteria applied to the request. Each step in Table 5C refers to a check that was applied to the transaction, the results of the check, and the user answer provided at the time the request was entered in the PA online application portal. The table also shows how authorization proceeded by indicating the next step to apply when the current step is completed. The data provided in Table 5C varies according to the drug flow applicable to the requested drug.

TABLE 5C

PA Request Detail Page - Evaluation Criteria

| Step | Result | User Answer | Next Step |
|---|---|---|---|
| 579 Medicare request | Medicare | A - Medicare | 581 |
| 581 Patient age | Age over 12 | A - 78 | 582 |
| 582 Drug within MDL database | Within MDL database | A - 30/30 | 585 |
| 583 Diagnosis Title | | | 0 |

TABLE 5C-continued

PA Request Detail Page - Evaluation Criteria

| Step | Result | User Answer | Next Step |
|---|---|---|---|
| 584 Diagnosis | | | 0 |
| 585 Diagnosis-Zollinger | Not Zollinger Ellison | A | 586 |
| 586 Diagnosis-Barrett | Not Barrett's Esophagus | A | 587 |
| 587 Diagnosis-Erosive Esophagitis | Erosive Esophagitis | A - Erosive Esophagitis | -6 |
| 588 Diagnosis-Esophageal Stricture | Not Esophageal Stricture | | 589 |
| 589 Diagnosis-Esophageal Shortening | Not Esophageal Shortening | | 591 |
| 590 Diagnosis-Gastritis | | | -2 |
| 591 Diagnosis-Cancer | Not Cancer | | 592 |
| 592 Diagnosis-LPR | Not LPR | | 601 |
| 593 GERD | Not GERD | | -2 |
| 594 PUD | Not PUD | | -2 |
| 595 Diagnosis-Other | Not Other | | -2 |
| 596 ICD-9 Code | ICD-9 Code | AN - Test2 | -2 |
| 597 Unconfirmed Diagnosis Title | | | 0 |
| 598 Unconfirmed-Dysphasia | Not Dysphasia | | -2 |
| 599 Unconfirmed-Weight Loss | Weight Loss | AN - Weight Loss | -2 |
| 641 Other Medications Title | | | 0 |
| 642 Other Medications Group | | | 0 |
| 643 OtherMed-Coumadin | Not Coumadin | | -2 |
| 644 OtherMed-Ticlid/Plavix | Ticlid/Plavix | | -2 |
| 645 OtherMed-Bisphophonates | Not Bisphophonates | | -2 |
| 645 OtherMed-Antineoplastic Meds | Not Antineoplastic Meds | | -2 |
| 647 OtherMed-Chronis Oral Steroids | Not Chronis Oral Steroids | | -2 |
| 648 OtherMed-Chronic NSAIDS | Not Chronic NSAIDS | | -2 |
| 649 OtherMed-Heparin Products | Not Heparin Products | | -2 |
| 639 Tried/Failed 2/3 | Not tried/failed 2/3 | AN - No | -2 |
| 650 Additional Information | Additional Information | AN - Test5 | -2 |

Finally, the bottom portion of the page provides a legend for interpreting the page details. The legend provides a guide to showing the user which answers were and were not used in the PA decision process as which answers were not answered or applicable to the PA decision process. The table also explains the decision codes.

TABLE 5D

PA Request Detail Page - Legend

Legend:

| | |
|---|---|
| A | Answer used in the decision process |
| AN | Answer not used in the decision process |
| Blank | Unanswered or not applicable |

Decision Steps:

| | |
|---|---|
| -1 | Authorization not needed 01 already available |
| -2 | Not approved |
| -3 | Authorize for 3 months |
| -4 | Authorize for 6 months |
| -5 | Authorize for 1 year |
| -6 | Authorize indefinitely |
| -7 | Not Approved by HCPR |
| -8 | Healthcare Provider Record - Authorize for 3 months |
| -9 | Healthcare Provider Record - Authorize for 6 months |
| -10 | Healthcare Provider Record - Authorize for 1 year |
| -11 | Healthcare Provider Record - Authorize Indefinitely |

A web-based maintenance interface to the online application supports modifications and additions to the drug list as well as questions that are used to determine whether a drug request meets authorization criteria. New drugs and attendant authorization criteria may be added to the list for processing through the auto-approval PA application. Details of the maintenance interface are provided in Tables 6-8.

Table 6 shows details of a flow maintenance page that allows a user to select and revise drug flows related to prior authorization according to the present invention.

TABLE 6

Flow Maintenance Details

| Flow Name | Version | Modified |
|---|---|---|
| ADHD | 2.03 - Phase 2 ADHD | 6/6/2007 9:18:15 PM |
| MS | 2.07 - Phase 2 MS | 6/6/2007 9:18:58 PM |
| Urinary | 2.05 - Phase 2 Urinary | 6/6/2007 9:20:27 PM |
| Byetta | 2.10 - Byetta 2007-06-12, split from Januvia | 6/14/2007 7:52:30 AM |
| Januvia/Janumet | 2.10 - Januvia/Janumet 2007-06-12, split from Byetta | 6/14/2007 7:52:15 AM |
| Anti-epileptics 2008 | 3.00 - Anti-epileptics 2008 | 12/31/2007 11:40:43 AM |
| Lamisil/Penlac/Sporanox 2008 | 3.00 - Phase 3 Antifungal Lamisil/Penlac/Sporanox | 12/31/2007 11:41:22 AM |
| Ultram/Ultram ER 2008 | 3.00 - Ultram/Ultram ER 2008 | 12/31/2007 11:42:26 AM |

Maintenance features and functionality also include the ability to maintain a list of PA drugs. Table 7 shows details of a drug maintenance page that allows a user to select and revise drug flows related to prior authorization according to the present invention.

TABLE 7

Drug Maintenance Details

| Label Name | GCN | Flow |
|---|---|---|
| ACCUPRIL 5 MG TABLET | 27572 | Heart/BP 2008 |
| ACCUPRIL 10 MG TABLET | 27570 | Heart/BP 2008 |
| ACCUPRIL20 MG TABLET | 27571 | Heart/BP 2008 |
| ACCUPRIL 40 MG TABLET | 27573 | Heart/BP 2008 |
| ACCURETIC 10-12.5 MG TABLET | 54160 | Heart/BP 2008 |
| ACEON 2 MG TABLET | 13758 | Heart/BP 2008 |
| ACEON 4 MG TABLET | 13759 | Heart/BP 2008 |
| ACEON 8 MG TABLET | 93207 | Heart/BP 2008 |

TABLE 7-continued

Drug Maintenance Details

| Label Name | GCN | Flow |
|---|---|---|
| APAP/BUTALBITAL325/50 TAB | 72711 | Pain Medications 2008 |
| ACIPHEX 20 MG TABLET EC | 94639 | PPI/Heartburn 2008 |
| ACTIQ 200 MCG LOZENGE | 19204 | Pain Medications 2008 |
| ACTIQ 400 MCG LOZENGE | 19206 | Pain Medications 2008 |
| ACTIQ 600 MCG LOZENGE | 19191 | Pain Medications 2008 |
| ACTIQ 800 MCG LOZENGE | 19192 | Pain Medications 2008 |
| ACTIQ 1,200 MCG LOZENGE | 19193 | Pain Medications 2008 |
| ACTIQ 1,600 MCG LOZENGE | 19194 | Pain Medications 2008 |
| ACUFLEX CAPLET | 22832 | Pain Medications 2008 |
| ADALAT CC 30 MG TABLET | 02226 | Heart/BP 2008 |
| ADALAT CC 60 MG TABLET | 02227 | Heart/BP 2008 |
| ADALAT CC 90 MG TABLET | 02228 | Heart/BP 2008 |

Maintenance features and functionality also include the ability to maintain a list of PA messages. Table 8 shows details of a message maintenance page that allows a user to select and revise message codes and related messages that are used in a PA online application according to the present invention.

TABLE 8

PA Message Maintenance Details

| Message Code | Description |
|---|---|
| Approved.1Year | One year |
| Approved.3Months | Three months |
| Approved.6Months | Six months |
| Approved.99Years | Indefinitely |
| Approved.Already | Approval is not needed or has previously been granted. |
| Approved.Approved | APPROVED |
| Approved.Confirmation | Confirmation # {0} |
| Approved.Coverage | Coverage and eligibility will be determined at the time the prescription is filled in accordance with all applicable provisions of the contract. |
| Approved.Disclaimer | Company does not notify the patient or pharmacy. Please note that this approval will be valid for {0} subject to the length of the member's coverage under Humana, and as long as there is a valid prescription. |
| Approve.Message | Your Prior Authorization Request for {0} for {1} has been successfully submitted and approved. {1} can now have {0} filled at a pharmacy. |
| Approved.PrintCopy | Print a Copy for Patient Records |
| Approved.Reference | Reference # {0} |

Appendix A provides details regarding drug flows and lists HTML code for a sample drug flow related to heartburn. In this example, the code processes the drug information and category/reason/disposition metrics for PPI-Heartburn drugs in PA. The drug selection page uses the drug information. The steps of the process are based a list of decision questions that may be provided in a flow chart or other document from a review team. The drug flow pages use this information to generate a questionnaire. The results are effectively a decision tree. Each step has one or more next steps based on the possibly answers. The final step is one of "available," "approved/denied," or "approved 3 months, 6 months, 1 year or indefinitely."

PAs auto approved through the online application of the present invention reduce the work load for current clinical pharmacy review division staff. The present invention allows many PA requests to be auto-approved without input from a clinical pharmacy review division. For requests that are not auto-approved, the present invention integrates claims and medical history information as well notes into the drug request transaction computer system transactions to facilitate clinical pharmacy review and expedite the customer's PA allowing him or her to get a needed medication sooner. The present invention transforms the consumer experience by increasing efficiency and timeliness in approving PAs for pharmacy benefits or network provider members. The ease of requesting online approvals for PA drug requests also results in greater efficiency in physician and other medical service provider offices.

Although the PA process of the present invention has been described in relation to processing at a pharmacy benefits manager computer and pharmacy benefits computer, it is understood that one or computers may be used to complete processing at the various stages of the approval process. While certain embodiments of the present invention are described in detail above, the scope of the invention is not to be considered limited by such disclosure, and modifications are possible without departing from the spirit of the invention as evidenced by the following claims:

What is claimed is:

1. A computerized method for processing prior authorization drug requests comprising:
   (a) receiving at a rules database server an electronic prior authorization drug request, said request comprising:
      (1) identifying information for a member of a pharmacy benefits plan and identifying information for a drug prescribed to said member; and
      (2) identifying information for a prescribing physician submitting said electronic prior authorization drug request for said member;
   (b) assigning a reference identifier to said prior authorization drug request;
   (c) logging said electronic prior authorization drug request with said reference identifier in a drug request transaction computer system;
   (d) applying at said transaction computer system authorization criteria to said electronic prior authorization drug request to reach a prior authorization decision approving or denying dispensing of said drug to said member according to said pharmacy benefits plan for said member and said identifying information for said member;
   (e) updating said electronic prior authorization drug request in said drug request transaction computer system according to said prior authorization decision;
   (f) if said prior authorization drug request is automatically approved, forwarding said electronic prior authorization drug request from said rules database server to a pharmacy benefits manager computer to facilitate dispensing of said drug to said member; and
   (g) if said prior authorization drug request is automatically denied, providing a computer user with access to said prior authorization request in said drug request transaction computer system.

2. The method of claim 1 wherein said identifying information for said drug prescribed to said member comprises a drug identifier, a quantity, a quantity per days value, and a number of refills.

3. The method of claim 1 wherein applying authorization criteria to said drug request comprises application of said authorization criteria by a software application at said rules database server.

4. The method of claim 1 wherein providing a computer user with access to said prior authorization request comprises providing a clinical pharmacy review representative with access to said request in said drug request transaction computer system to permit said representative to complete a prior authorization review.

5. The method of claim 4 further comprising updating said electronic prior authorization drug request logged in said drug request transaction computer system with a prior authorization approval if said representative determines said request meets said authorization criteria.

6. The method of claim 1 wherein said prior authorization drug request is for a drug selected from the group consisting of proton pump inhibitors and heartburn drugs, cox-2 inhibitor drugs, non-steroid antiinflammatory drugs, type-2 diabetes drugs, and nail fungus treatment drugs.

7. The method of claim 1 wherein said prior authorization decision is selected from the group consisting of approved, not approved, and approval not required.

8. A computerized method for processing prior authorization drug requests comprising:
   (a) receiving from a pharmacy benefits manager at a rules database server an electronic prior authorization drug request to complete a prior authorization process for a prescription drug that requires prior authorization, said request comprising:
      (1) identifying information for a member of a pharmacy benefits plan and identifying information for a drug prescribed to said member; and
      (2) identifying information for a prescribing physician submitting said electronic prior authorization drug request for said member;
   (b) at said rules database server, applying a prior authorization process comprising:
      (i) assigning a reference identifier to said electronic request;
      (ii) adding said electronic request with said reference identifier to a drug request transaction computer system;
      (iii) applying authorization criteria to said electronic request to reach a prior authorization decision approving or denying dispensing of said drug to said member according to said pharmacy benefits plan for said member and said identifying information for said member;
      (iv) if said electronic request meets said authorization criteria, forwarding an electronic prior authorization approval to said pharmacy benefits manager computer; and
      (v) if said electronic request does not meet said authorization criteria, providing a computer user with access to said prior authorization request in said drug request transaction computer system.

9. The method of claim 8 wherein said drug identifying information comprises a drug identifier, a quantity, a quantity per days value, and a number of refills.

10. The method of claim 8 wherein providing a computer user with access to said prior authorization request comprises providing a clinical pharmacy review representative with access to said request to permit said representative to determine if said request meets said authorization criteria.

11. The method of claim 10 further comprising permitting said clinical pharmacy review representative to access said electronic request in said drug request transaction computer system using said reference identifier.

12. The method of claim 11 further comprising updating said electronic request logged in said drug request transaction computer system with a prior authorization approval if said representative determines said request meets said authorization criteria.

13. The method of claim 8 wherein said electronic request is for a drug selected from the group consisting of proton pump inhibitors and heartburn drugs, cox-2 inhibitor drugs, non-steroid antiinflammatory drugs, type-2 diabetes drugs, and nail fungus treatment drugs.

14. The method of claim 8 wherein receiving an electronic request for a prescription drug to be dispensed to a member comprises receiving said electronic request from a device selected from the group consisting of a physician office computer, a physician office handheld device, and a pharmacy point-of-sale computer.

15. The method of claim 8 wherein said electronic request further comprises a prescription claim history for said member.

16. The method of claim 11 wherein said electronic request logged in said drug request transaction computer system further comprises a medical claim history for said member.

17. The method of claim 11 further comprising updating said electronic request in said drug request transaction computer system with a denial decision if said clinical pharmacy representative determines said request does not meet said authorization criteria.

* * * * *